(12) United States Patent
Rodjegard et al.

(10) Patent No.: US 12,216,104 B2
(45) Date of Patent: Feb. 4, 2025

(54) IN-VEHICLE ABNORMALITY DETECTION DEVICE AND IN-VEHICLE ABNORMALITY DETECTION METHOD

(71) Applicant: ASAHI KASEI MICRODEVICES CORPORATION, Tokyo (JP)

(72) Inventors: Henrik Rodjegard, Delsbo (SE); Yuji Goda, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 446 days.

(21) Appl. No.: 17/773,108

(22) PCT Filed: Nov. 5, 2020

(86) PCT No.: PCT/JP2020/041409
§ 371 (c)(1),
(2) Date: Apr. 29, 2022

(87) PCT Pub. No.: WO2021/090892
PCT Pub. Date: May 14, 2021

(65) Prior Publication Data
US 2022/0373526 A1    Nov. 24, 2022

(30) Foreign Application Priority Data
Nov. 8, 2019    (JP) .................... 2019-203314

(51) Int. Cl.
*G01N 33/00* (2006.01)
*B60H 1/00* (2006.01)

(52) U.S. Cl.
CPC ....... *G01N 33/004* (2013.01); *B60H 1/00742* (2013.01); *B60H 1/008* (2013.01)

(58) Field of Classification Search
CPC ... G01N 33/004; B60H 1/00742; B60H 1/008
See application file for complete search history.

(56) References Cited

U.S. PATENT DOCUMENTS

| | | |
|---|---|---|
| 6,344,798 B1 | 2/2002 | Schell |
| 6,424,267 B1 | 7/2002 | Schell |

(Continued)

FOREIGN PATENT DOCUMENTS

| | | |
|---|---|---|
| CN | 105701980 A | 6/2016 |
| CN | 107364307 A | 11/2017 |

(Continued)

OTHER PUBLICATIONS

Jung, Heejung, "Modeling CO2 Concentrations in Vehicle Cabin" SAE International, 2013-01-1497, Apr. 8, 2013. (Year: 2013).*

(Continued)

*Primary Examiner* — Paul M. West
(74) *Attorney, Agent, or Firm* — Morgan, Lewis & Bockius LLP

(57) ABSTRACT

A change rate of in-vehicle carbon dioxide concentration at an optional time point when the vehicle is in a parked state is estimated on the basis of detection signals of a $CO_2$ concentration sensor at two different time points when in the parked state; and on the basis of a detection signal of the $CO_2$ concentration sensor at the optional time point, a preset time constant of concentration change of the in-vehicle carbon dioxide concentration, and the estimated change rate, the in-vehicle carbon dioxide concentration at a time point when a predetermined time according to the time constant has elapsed since the optional time point is estimated (steps S4 to S7). A detection target organism is determined to be present in the vehicle when the estimated in-vehicle carbon dioxide concentration is equal to or more than a threshold value set according to the detection target organism (steps S8 and S9).

18 Claims, 8 Drawing Sheets

(56) References Cited

U.S. PATENT DOCUMENTS

| | | | |
|---|---|---|---|
| 7,109,853 | B1 | 9/2006 | Mattson et al. |
| 10,169,975 | B1 | 1/2019 | Payment |
| 2008/0211668 | A1 | 9/2008 | Dixon et al. |
| 2008/0268761 | A1 | 10/2008 | Iida et al. |
| 2014/0278145 | A1 | 9/2014 | Angeli et al. |
| 2016/0103111 | A1 | 4/2016 | Griffin |
| 2016/0356752 | A1 | 12/2016 | Yocum |
| 2017/0294100 | A1 | 10/2017 | Haskew et al. |
| 2018/0072299 | A1* | 3/2018 | Soifer ................ B60H 1/00978 |

FOREIGN PATENT DOCUMENTS

| | | | |
|---|---|---|---|
| JP | 2001-229476 | A | 8/2001 |
| JP | 2004-531721 | A | 10/2004 |
| JP | 2008-273394 | A | 11/2008 |
| JP | 2009-090906 | A | 4/2009 |
| JP | 2017-003203 | A | 1/2017 |
| JP | 2017-016185 | A | 1/2017 |
| JP | 2017-117411 | A | 6/2017 |
| JP | 2019-168858 | A | 10/2019 |

OTHER PUBLICATIONS

International Search Report issued in corresponding International Patent Application No. PCT/JP2020/041409 dated Jan. 26, 2021.
International Preliminary Report on Patentability issued in corresponding International Patent Application No. PCT/JP2020/041409 dated May 10, 2022.

* cited by examiner

… (1)

IN-VEHICLE ABNORMALITY DETECTION DEVICE AND IN-VEHICLE ABNORMALITY DETECTION METHOD

TECHNICAL FIELD

The present invention relates to an in-vehicle abnormality detection device and an in-vehicle abnormality detection method.

BACKGROUND ART

As a device for detecting the presence of an organism such as a person or an animal in a vehicle, methods have been proposed such as detecting carbon dioxide concentration (hereinafter referred to also as $CO_2$ concentration) in a vehicle and detecting the presence of an organism by detecting movements caused by heartbeat and breathing using a millimeter-wave radar.

An example of such proposed methods for detecting an organism using $CO_2$ concentration is to determine the presence of an organism when $CO_2$ concentration or $CO_2$ increase rate in a vehicle exceeds a threshold value (see, for example, PTL 1). Other methods have also been proposed such as detecting the number of people present in a vehicle on the basis of $CO_2$ concentration (see, for example, PTL 2) and furthermore a device for detecting a misplaced child on the basis of $CO_2$ concentration (see, for example, NPL 1).

CITATION LIST

Patent Literature

PTL 1: US 2016/0103111 A1
PTL 2: 2014/0278145 A1

Non Patent Literature

NPL 1: PAYTON'S CHARM, Retrieved from the Internet, URL: <https://paytonscharm.com/>

SUMMARY OF INVENTION

Technical Problem

In the method for determining the presence of an organism in a vehicle when $CO_2$ concentration or $CO_2$ increase rate in a vehicle exceeds a threshold value, the threshold value needs to be preset. For example, the threshold value is set by actually measuring the $CO_2$ concentration or other means. However, it takes time for the $CO_2$ concentration to actually reach a value equivalent to the threshold value, and there are also significant individual differences. Due to that, in order to set an appropriate threshold value in consideration of individual differences, it is necessary to actually measure $CO_2$ concentrations with respect to a plurality of persons and set one or more threshold values corresponding to the plurality of persons from a plurality of measurement results. This is time-consuming to set the threshold values. Particularly, setting a threshold value for detecting the presence of a child or baby requires leaving the child or baby for long hours in an environment equivalent to such a situation that the child or baby is actually confined in a vehicle. Therefore, it is difficult to measure $CO_2$ concentration over long hours.

Additionally, the $CO_2$ concentration in the vehicle changes not only due to the amount of $CO_2$ emitted by the child or baby present in the vehicle but also due to the vehicle's airtightness, and the airtightness deteriorates over time. Thus, there has been a desire for a detection method that allows for more accurate detection of the presence of a child in a vehicle.

Accordingly, the present invention has been made with a focus on the above conventional unsolved problems. An object of the present invention is to provide an in-vehicle abnormality detection device and an in-vehicle abnormality detection method that allow for more accurate detection of the presence of an organism in a vehicle.

Solution to Problem

An in-vehicle abnormality detection device according to an embodiment of the present invention includes: a $CO_2$ concentration sensor configured to detect in-vehicle carbon dioxide concentration of a vehicle; a parked state detection unit configured to detect that the vehicle is in a parked state; a time constant storage unit configured to store a time constant $\tau$ of concentration change of the in-vehicle carbon dioxide concentration; a change rate estimation unit configured to, on a basis of detection signals $C(t1)$ and $C(t2)$ of the $CO_2$ concentration sensor at two different time points t1 and t2 when the parked state is detected by the parked state detection unit, estimate a change rate of the in-vehicle carbon dioxide concentration at a time point t when the parked state is detected; a carbon dioxide concentration estimation unit configured to estimate a carbon dioxide concentration estimation value C0 in the vehicle at a time point when a predetermined time has elapsed since the time point t on a basis of a detection signal $C(t)$ of the $CO_2$ concentration sensor at the time point t, the time constant $\tau$ stored in the time constant storage unit, and the change rate estimated by the change rate estimation unit; and an abnormality determination unit configured to determine that there is a detection target organism present in the vehicle when the carbon dioxide concentration estimation value C0 estimated by the carbon dioxide concentration estimation unit is equal to or more than a threshold value set according to the detection target organism. Hereinafter, when the time point t and a symbol representing a similar time point are used with an operator, the t and the symbol represent a time at the time point.

Additionally, an in-vehicle abnormality detection method according to another embodiment of the present invention includes: detecting in-vehicle carbon dioxide concentration of a vehicle when in a parked state by a $CO_2$ concentration sensor; estimating a change rate of the in-vehicle carbon dioxide concentration at an optional time point when in the parked state on a basis of detection signals of the $CO_2$ concentration sensor at two different time points when in the parked state; estimating, on a basis of a detection signal of the $CO_2$ concentration sensor at the optional time point, a time constant of concentration change of the in-vehicle carbon dioxide concentration, and the estimated change rate, the in-vehicle carbon dioxide concentration at a time point when a predetermined time according to the time constant has elapsed since the optional time point; and determining that there is a detection target organism present in the vehicle when the estimated in-vehicle carbon dioxide concentration is equal to or more than a threshold value set according to the detection target organism.

In addition, an in-vehicle abnormality detection device according to another embodiment of the present invention includes: a $CO_2$ concentration sensor configured to detect in-vehicle carbon dioxide concentration of a vehicle; a parked state detection unit configured to detect that the vehicle is in a parked state; a time constant storage unit configured to store a time constant τ of concentration change of the in-vehicle carbon dioxide concentration; a change rate estimation unit configured to, on a basis of detection signals C(t1) and C(t2) of the $CO_2$ concentration sensor at two different time points t1 and t2 (provided that t2>t1) when the parked state is detected by the parked state detection unit, estimate a change rate dC(t)/dt of the in-vehicle carbon dioxide concentration at a time point t when the parked state is detected; a threshold value determination unit configured to determine a threshold value Vth on a basis of a detection signal C(t3) of the $CO_2$ concentration sensor at a time point t3 when the parked state is detected by the parked state detection unit, the time constant τ stored in the time constant storage unit, and an outside-vehicle $CO_2$ concentration Coutdoor; and an abnormality determination unit configured to determine whether there is a detection target organism present in the vehicle according to a result of a comparison between the change rate of the carbon dioxide concentration estimated by the change rate estimation unit and the threshold value Vth determined by the threshold value determination unit.

Furthermore, an in-vehicle abnormality detection method according to another embodiment of the present invention includes: detecting in-vehicle carbon dioxide concentration of a vehicle when in a parked state by a $CO_2$ concentration sensor; estimating a change rate of the in-vehicle carbon dioxide concentration at an optional time point when in the parked state on a basis of detection signals of the $CO_2$ concentration sensor at two different time points when in the parked state; determining a threshold value Vth of the change rate of the in-vehicle carbon dioxide concentration on a basis of a detection signal of the $CO_2$ concentration sensor at the optional time point, a time constant of concentration change of the in-vehicle carbon dioxide concentration, and an outside-vehicle $CO_2$ concentration Coutdoor; and determining whether there is a detection target organism present in the vehicle by comparing the estimated change rate of the in-vehicle carbon dioxide concentration with the threshold value Vth.

Advantageous Effects of Invention

According to an aspect of the present invention, the presence or absence of an organism in a vehicle can be detected with higher accuracy.

DESCRIPTION OF EMBODIMENTS

Next, embodiments of the present invention are described with reference to the drawings. In the following description of the drawings, the same or similar portions are denoted by the same or similar reference signs. Additionally, the embodiments given below exemplify devices and methods for embodying the technological concept of the present invention, and which concept does not limit structures, arrangements, and the like of components of the present invention to those described below. Various modifications can be added to the technological concept of the present invention within the technological scope defined in the appended claims.

First Embodiment

Configuration of In-Vehicle Abnormality Detection Device 1

Figure 1:
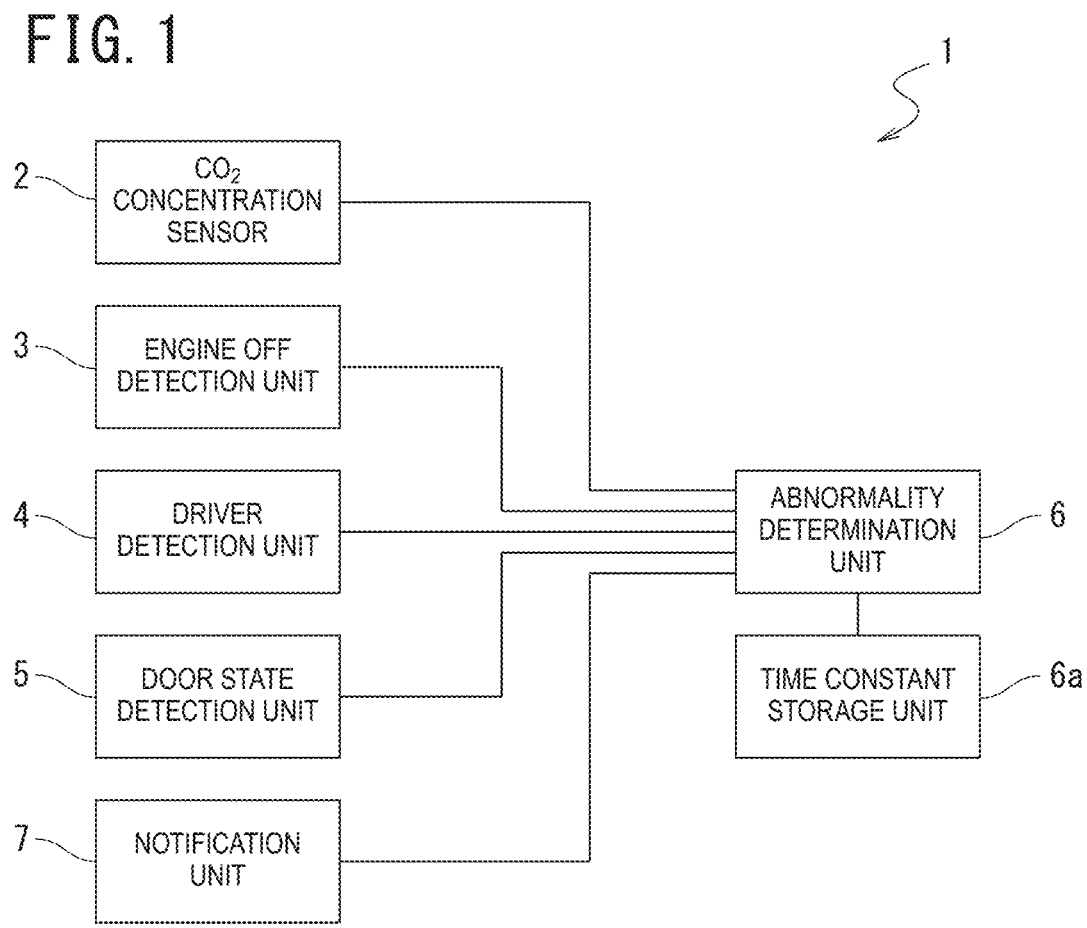
FIG. 1 is a schematic configuration diagram illustrating an example of an in-vehicle abnormality detection device according to the first embodiment of the present invention.

FIG. 1 is a schematic configuration diagram illustrating an example of an in-vehicle abnormality detection device according to the first embodiment of the present invention.

An in-vehicle abnormality detection device 1 includes a $CO_2$ concentration sensor 2 that detects carbon dioxide concentration, an engine off detection unit 3 that detects an engine off state, a driver detection unit 4 that detects the absence of a driver in a vehicle, a door state detection unit 5 that detects that all doors of the vehicle are closed, an abnormality detection unit 6 that estimates a carbon dioxide concentration C0 (hereinafter referred to also as $CO_2$ concentration estimation value C0) in the vehicle when assuming that the vehicle is in a steady state on the basis of a detection signal of each of the above units and detects whether there is an organism present in the vehicle on the basis of the estimated carbon dioxide concentration estimation value C0, and a notification unit 7 that notifies that there is an organism present in the vehicle when the abnormality determination unit 6 detects the presence of the organism in the vehicle.

Figure 2:
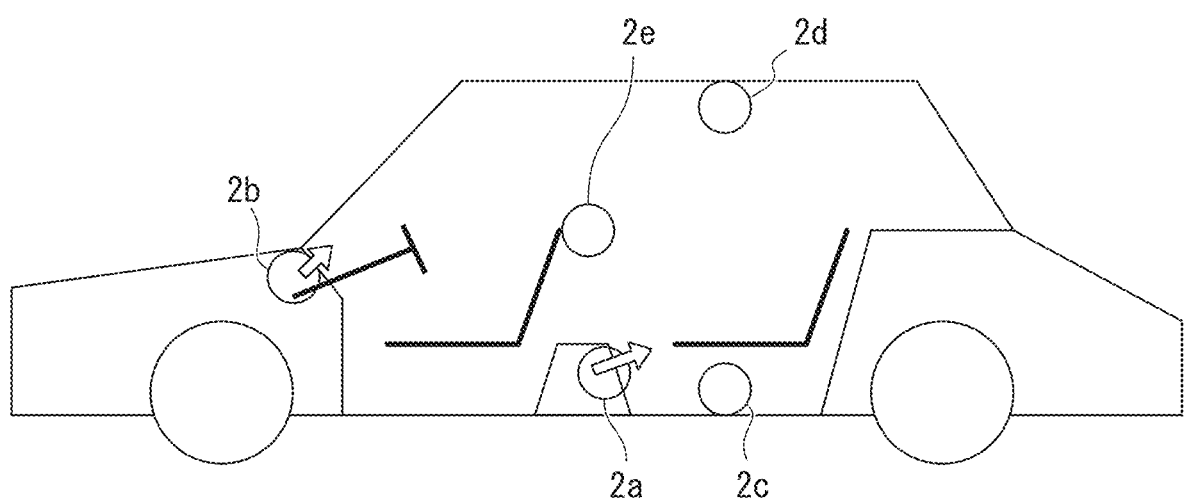
FIG. 2 is an arrangement diagram illustrating an example of an arrangement position of a $CO_2$ concentration sensor.

The $CO_2$ concentration sensor 2 can be provided immediately behind an air intake port (not illustrated) provided on the bottom of a vehicle body, as illustrated by 2a of FIG. 2. When the $CO_2$ concentration sensor 2 is provided near the air intake port in this way, the intake of outside air through an activated outside air fan allows a detection signal of the $CO_2$ concentration sensor 2 to have a value approximately equivalent to a $CO_2$ concentration of the outside air. Therefore, by correcting a time constant t that will be described later using the detection signal equivalent to the $CO_2$ concentration of the outside air, estimation accuracy of the $CO_2$ concentration estimation value C0 can be improved.

In addition, as illustrated by 2b of FIG. 2, the $CO_2$ concentration sensor 2 may be provided near an air vent on the top of a dashboard. In this case as well, using the detection signal of the $CO_2$ concentration sensor 2 output in the state where the outside air is taken in through the activated outside air fan allows for improved estimation accuracy of the $CO_2$ concentration estimation value C0.

As illustrated by 2c of FIG. 2, the $CO_2$ concentration sensor 2 may be provided near a floor in the vehicle. When it is warm inside the vehicle, exhaled air may collect in a lower part inside the vehicle due to a relationship between in-vehicle temperature and exhalation temperature. Providing the $CO_2$ concentration sensor 2 near the floor in the vehicle allows for prompt detection of changes in $CO_2$ concentration due to exhalation.

Additionally, the $CO_2$ concentration sensor 2 may be provided on a ceiling in the vehicle, as illustrated by 2*d* of FIG. 2. When it is cold inside the vehicle, exhaled air may collect in an upper part inside the vehicle due to the relationship between in-vehicle temperature and exhalation temperature. Providing the $CO_2$ concentration sensor 2 on the ceiling in the vehicle allows for prompt detection of changes in $CO_2$ concentration due to exhalation.

Furthermore, as illustrated by 2*e* of FIG. 2, the $CO_2$ concentration sensor 2 may be provided at a center position in the vehicle, i.e., a position that is substantially in the center of a front-rear direction and a left-right direction. Providing the $CO_2$ concentration sensor 2 at the position substantially in the center in the vehicle allows the presence or absence of an organism to be detected in the same amount of time regardless of a location of the organism in the vehicle.

The $CO_2$ concentration sensor 2 may also be arranged at any plurality of locations among the 2*a* to the 2*e*, whereby $CO_2$ concentration in the vehicle may be estimated from detection signals of the plurality of $CO_2$ concentration sensors 2, and the estimated $CO_2$ concentration may be used to perform determination processing that will be described later. Using the detection signals of the plurality of $CO_2$ concentration sensors 2 arranged at the different positions in the vehicle in this way allows for more accurate and more prompt detection of changes in the $CO_2$ concentration due to the exhalation of an organism present in the vehicle.

Furthermore, a circulation fan may be activated in the state where the $CO_2$ concentration sensor 2 is provided at each of the locations 2*a* to 2*e*. Activating the circulation fan and mixing air inside the vehicle can suppress variations in the $CO_2$ concentration due to the arrangement position of the $CO_2$ concentration sensor 2 and a buoyancy of the $CO_2$.

The engine off detection unit 3 is a sensor that detects that the engine is stopped, and determines that the engine is in the stopped state when it detects that "LOCK" is selected in an ignition switch, for example.

The driver detection unit 4 is a sensor that detects that the driver is in the driver's seat. For example, a pressure sensor is provided on the driver's seat, and it is detected whether the driver is seated or not from a detection value of the pressure sensor.

The door state detection unit 5 is a sensor that detects that all doors on the vehicle are in the closed state. For example, the doors' closed state may be detected by providing, on each door, a switch that is turned on when the door is closed. In the case of a vehicle with a rear door, it is detected that all doors including the rear door are closed.

The abnormality detection unit 6 inputs the detection signals of the engine off detection unit 3, the driver detection unit 4, and the door state detection unit 5, and detects whether there is an organism in the vehicle when the engine is off, the driver is not in the driver's seat, and all the doors are closed, i.e., when it is determined that the vehicle is in a parked state. Specifically, the abnormality detection unit 6 estimates the $CO_2$ concentration estimation value C0 on the basis of the detection signal of the $CO_2$ concentration sensor 2 and the time constant t previously stored in a time constant storage unit 6*a*, and determines whether there is an organism present in the vehicle on the basis of the estimated $CO_2$ concentration estimation value C0. The $CO_2$ concentration estimation value C0 is estimated using the following Formula (1) on the basis of a detection signal of the $CO_2$ concentration sensor 2 at a present time point t. Note that t1 and t2 in Formula (1) represent two different time points when it is determined that the vehicle is in the parked state, in which the time point t2 represents a time point that is later than the time point t1. Additionally, C(t1) and C(t2), respectively, represent a detection signal of the $CO_2$ concentration sensor 2 detected at the time point t1 and a detection signal of the $CO_2$ concentration sensor 2 detected at the time point t2.

$$C0 = C(t) + \tau \times dC(t)/dt$$

$$dC(t)/dt = [C(t2) - C(t1)]/(t2 - t1) \qquad (1)$$

Note that the time constant $\tau$ is a time constant that is determined by volume inside the vehicle and airtightness inside the vehicle, and is a time constant of concentration change of carbon dioxide concentration in the vehicle. The time constant $\tau$ is preset by an experiment or the like and stored in the time constant storage unit 6*a*. Additionally, the time constant $\tau$ is updated on the basis of the detection signal of the $CO_2$ concentration sensor 2 in a process in which determination processing that will be described later is executed. dC(t)/dt represents the amount of change per unit time in a detection signal C(t) of the $CO_2$ concentration at the time point t. In Formula (1), a change rate per unit time in the detection signal C(t) of the $CO_2$ concentration at the optional time point t when the vehicle is in the parked state is obtained from the detection signals C(t1) and C(t2) of the $CO_2$ concentration sensor 2 at the time points t1 and t2 when the vehicle is in the parked state (a change rate estimation unit).

In addition, when the abnormality determination unit 6 determines that there is an organism present in the vehicle, the notification unit 7 is activated to notify of the presence of the organism in the vehicle.

The notification unit 7 is activated by the abnormality determination unit 6. Examples of the notification by the notification unit 7 include emitting an alarm sound, sounding the vehicle's horn, contacting by e-mail or SNS (social networking service) notification to the driver's cell phone or smart phone, and notifying via a vehicle-specific wireless service or an Internet access service.

Note that when it is determined that there is an organism in the vehicle, the abnormality determination unit 6 may be configured not only to activate the notification unit 7 but also, for example, to open a window of the vehicle and take in outside air. Alternatively, without providing the notification unit 7, the abnormality determination unit 6 may be configured to open the window of the vehicle or operate a cooling or heating function when it is determined that there is an organism in the vehicle.

Determination Processing by Abnormality Determination Unit 6

Next, an example of a processing procedure of the determination processing executed by the abnormality determination unit 6 is described with reference to a flowchart of FIG. 3.

The abnormality determination unit 6 executes the determination processing at a preset predetermined cycle, and first inputs the detection signals of the engine off detection unit 3, the driver detection unit 4, and the door state detection unit 5 (step S1). Then, when it is not detected that the engine is off, the driver is not in the driver's seat, and all the doors are closed (step S2), the processing ends as it is, whereas when all of the above conditions are satisfied, it is considered that the vehicle is in a parked state, and the processing proceeds to step S3 (a parked state detection unit). Then, a time point when a 5 second waiting time has elapsed since the determination of the parked state is defined as t=0, and the detection signal of the $CO_2$ concentration sensor 2 at the time point t=0 is read as C(0) (step S4). The waiting time in step S3 (5 seconds, here) is a time for measuring $CO_2$ concentration in the vehicle when the vehicle is parked with all the doors closed, i.e., an initial value of the $CO_2$ concentration in the vehicle, and is set to a time in which fluctuations in the $CO_2$ concentration in the vehicle due to opening and closing of the doors, stop of the circulation fan, disembarkation of the occupant(s), and the like accompanying the parking settle down, and it is possible to acquire an appropriate value as the initial value for the determination processing.

Next, the processing proceeds to step S5. When a 30 second waiting time has elapsed since the time point t=0, the processing proceeds to step S6, where a detection signal C(30 s) of the $CO_2$ concentration sensor 2 is read. The waiting time (30 seconds, here) in step S5 is set to a time in which it is possible to determine that a detection target organism is present in the vehicle from the degree of increase in the $CO_2$ concentration in the vehicle after parking with all the doors closed. Here, for example, the waiting time is set to 30 seconds as an example for a case where the detection target organism is a child, a pet, or the like.

Then, the processing proceeds to step S7, where according to Formula (1) above, the $CO_2$ concentration estimation value C0 is estimated from the following Formula (2) (a carbon dioxide concentration estimation unit).

$$C0=C(30\ s)+\{C(30\ s)-C(0)\}\times\tau/(30\ s) \quad (2)$$

Here, the $CO_2$ concentration in the vehicle varies depending on the amount of $CO_2$ emitted by the organism, but it also varies depending on airtightness in the vehicle and volume in the vehicle. Therefore, in the first embodiment, the $CO_2$ concentration estimation value C0 is estimated in consideration of the time constant $\tau$ determined by airtightness in the vehicle and volume in the vehicle, as indicated in Formula (2).

After estimating the $CO_2$ concentration estimation value C0 from Formula (2), the processing proceeds to step S8, where the estimated $CO_2$ concentration estimation value C0 is compared with a preset threshold value 3000 ppm. When the $CO_2$ concentration estimation value C0 is equal to or more than the threshold value (C0≥3000 ppm), it is determined that the detection target organism is present in the vehicle, and the notification unit 7 is activated to notify that the organism is present in the vehicle (step S9) (an abnormality determination unit). On the other hand, when the $CO_2$ concentration estimation value C0 is less than the threshold value 3000 ppm (C0<3000 ppm), the processing proceeds to step S10. Here, as an example for the case where the detection target organism is a child, a pet, or the like, the threshold value is set to 3000 ppm.

At step S10, a detection signal C (90 s) of the $CO_2$ concentration sensor 2 at a time point when a waiting time 60 s has elapsed since the time point when the $CO_2$ concentration estimation value C0 was estimated at step S7, i.e., a time point when 90 seconds have elapsed since the time point t=0 is read (step S11).

The waiting time 60 s in step S10 is set according to an estimation interval of the $CO_2$ concentration estimation value C0. Here, for example, as an example where the $CO_2$ concentration estimation value C0 is estimated at intervals of 60 seconds, the waiting time is set to approximately 60 seconds.

Next, the processing proceeds to step S12, where according to Formula (1) above, the $CO_2$ concentration estimation value C0 is estimated from the following Formula (3):

$$C0=C(90\ s)+\{C(90\ s)-C(0)\}\times\tau/(90\ s) \quad (3)$$

Then, the $CO_2$ concentration estimation value C0 estimated from Formula (3) is compared with the preset threshold value 3000 ppm. When the $CO_2$ concentration estimation value C0 is equal to or more than the threshold value 3000 ppm (C0≥3000 ppm) (step S13), it is determined that the detection target organism is present in the vehicle, and the notification unit 7 is activated to notify that the organism is present in the vehicle (step S14). On the other hand, when the $CO_2$ concentration estimation value C0 is less than the threshold value 3000 ppm (C0<3000 ppm), the processing proceeds to step S15.

Note that the threshold value 3000 ppm is a value that is preset by an experiment or the like, and the value is set to a $CO_2$ concentration at which it is possible to consider that the detection target organism is present in the vehicle with all the doors closed. For example, when detecting that there is a child present in the vehicle, the threshold value is set to approximately 3000 ppm.

Note that although at steps S7 and S12, the value (3000 ppm) at which it is possible to detect the presence of a child in the vehicle is set as the threshold value, the present invention is not limited thereto. For example, a plurality of threshold values may be set according to the type and the like of detection target organism, such as threshold values corresponding to not only a child but also a baby and threshold values corresponding to adults, and each of the plurality of threshold values may be compared with the $CO_2$ concentration estimation value C0 at the time point when the 30 second waiting time has elapsed since the time point when the parked state was determined and at the time point when the 90 second waiting time has elapsed since the time point when the parked state was determined. In this way, by setting the plurality of threshold values and comparing them with the $CO_2$ concentration estimation value C0, the type of an organism present in the vehicle, such as, for example, whether it is an adult or a child, can be detected from a magnitude of the threshold value when the $CO_2$ concentration estimation value C0 is equal to or more than the threshold value.

Here, when an organism is present in the vehicle with all the doors closed, the $CO_2$ concentration in the vehicle increases, so that the changing condition of the $CO_2$ concentration allows for detection of the presence of the organism. For example, when the $CO_2$ concentration estimation value C0 in the vehicle is equal to or more than the threshold value at step S7, the presence of the organism in the vehicle is notified at this time point. On the other hand, when the $CO_2$ concentration estimation value C0 in the vehicle is less than the threshold value at step S7 despite the presence of the organism in the vehicle, the presence of the organism in the vehicle is not notified at this time point. However, over time, exhalation of the organism present in the vehicle increases the $CO_2$ concentration in the vehicle. Therefore, at step S12, when the $CO_2$ concentration estimation value C0 becomes equal to or more than the threshold value, the presence of the organism in the vehicle is notified.

Thus, estimating the $CO_2$ concentration estimation value C0 twice, i.e., at the time point when 30 seconds have elapsed since the time point t=0 and at the time point when 90 seconds have elapsed from the time point t=0 and comparing with the threshold value can further ensure detection of the presence of the organism.

Note that here, the $CO_2$ concentration estimation value C0 and the threshold value are designed to be compared twice, but the number of times of the comparison is not limited thereto and may be three or more times. Additionally, the comparison between the $CO_2$ concentration estimation value C0 and the threshold value does not have to be made at the 60 second intervals, and may be performed at optional intervals.

At step S15, when a 210 second waiting time has elapsed since the time point when the $CO_2$ concentration estimation value C0 was estimated at step S12, the processing proceeds to step S16, where a detection signal C(300 s) of the $CO_2$ concentration sensor 2 is read. Then, at the time (step S17) when a 1 hour waiting time has elapsed since the time point when the detection signal C(300 s) of the $CO_2$ concentration sensor 2 was read at step S16, the processing proceeds to step S18, where a detection signal C(1 hour) of the $CO_2$ concentration sensor 2 at the time point when the 1 hour waiting time has elapsed since the reading of the detection signal C(300 s) of the $CO_2$ concentration sensor 2 at step S16 is read.

Next, at step S19 when a waiting time 300 s has elapsed since the reading of the detection signal C(1 hour) of the $CO_2$ concentration sensor 2 at step S18, a detection signal C(1 h+300 s) of the $CO_2$ concentration sensor 2 is read (step S20).

Then, the processing proceeds to step S21, where the time constant $\tau$ is updated from the detection signal C(0) of the $CO_2$ concentration sensor 2 detected at step S4, the detection signal C(300 s) of the $CO_2$ concentration sensor 2 detected at step S16, the detection signal (1 hour) of the $CO_2$ concentration sensor 2 detected at step S18, and the detection signal (1 hour+300 s) of the $CO_2$ concentration sensor 2 detected at step S20 using the following Formula (4) (a time constant updating unit). After that, the updated time constant $\tau$ is updated and stored in the time constant storage unit 6a. Then, the processing ends.

$$x=\{C(300\ s)-C(0)\}/\{C(1\ h+300\ s)-C(1\ h)\}$$

$$\tau=1\ \text{hour}/\ln(x)$$

$$\tau\text{new}=\tau\times 0.01+\tau\text{old}\times 0.99 \quad (4)$$

In other words, at steps S15 to S21, updating of the time constant $\tau$ is performed. Specifically, the time constant $\tau$ is updated on the basis of the amount of change "C(300 s)−C(0)" in the $CO_2$ concentration in the vehicle up to the time point when 300 seconds, i.e., 5 minutes have elapsed since the time point t=0 and the amount of change "C(1 h+300 s)−C(1 h)" in the $CO_2$ concentration in the vehicle up to the time point when 5 minutes have elapsed since the time point when 1 hour has elapsed since the calculation of the aforementioned amount of change. Note that here, although the time constant $\tau$ is updated on the basis of the amount of change in the $CO_2$ concentration in the vehicle in 5 minutes and the amount of change in the $CO_2$ concentration in the vehicle in 5 minutes after 1 hour therefrom, the amount of change in the $CO_2$ concentration in the vehicle is not limited to the amount of change in 5 minutes, and may be the amount of change in any time that allows the $CO_2$ concentration to change sufficiently. In addition, the interval for calculating the amount of change in the $CO_2$ concentration in the vehicle is not limited to 1 hour, and any interval may be set as long as the $CO_2$ concentration does not fall into an unchanged range.

Here, at the time point of step S15, it is determined that there is no organism present in the vehicle. Therefore, fluctuations in the $CO_2$ concentration in the vehicle are not affected by exhalation of $CO_2$ caused by an organism or the like, and can be regarded as those due to airtightness in the vehicle. Thus, setting the time constant $\tau$ on the basis of the detection signal of the $CO_2$ concentration sensor 2 in the state where the absence of an organism in the vehicle is determined allows for acquisition of the time constant $\tau$ that takes into account the airtightness in the vehicle at the present time.

Figure 3:
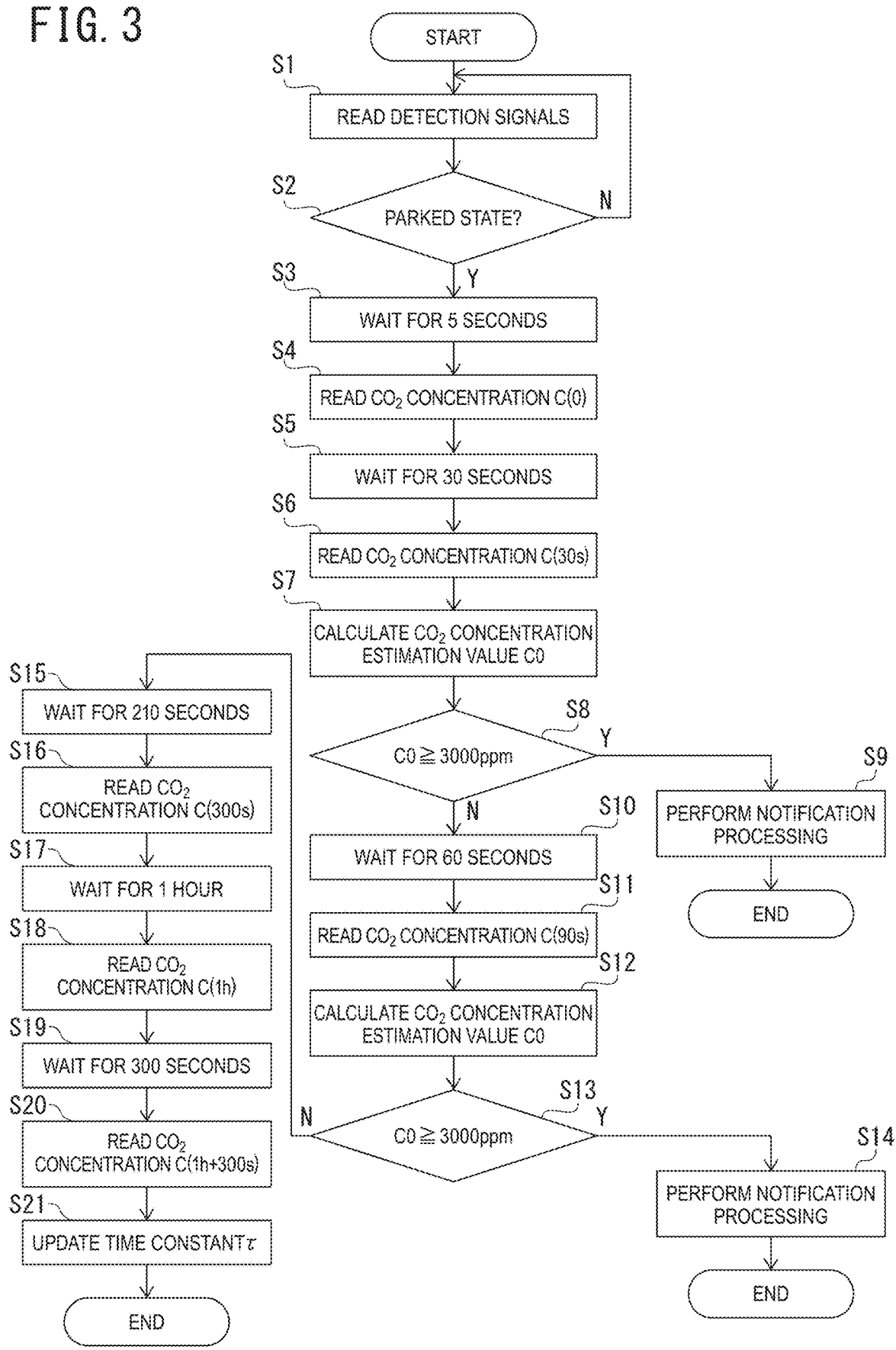
FIG. 3 is a flowchart illustrating an example of a processing procedure of determination processing.

Note that at step S2 in the flowchart of FIG. 3, after it is detected that the engine is off, the driver is not in the driver's seat, and all the doors are closed and thereby being determined that the vehicle is in the parked state, the processing of FIG. 3 is supposed to be ended when the conditions of step S2 are no longer satisfied i.e., when the engine is turned on, when the driver sits in the driver's seat, or when any of the doors is open.

Effects of In-Vehicle Abnormality Detection Device 1 According to First Embodiment The first embodiment uses the $CO_2$ concentration estimation value C0 as the $CO_2$ concentration in the vehicle. However, as a conventional method for detecting $CO_2$ concentration in a vehicle, there has been proposed a method of calculating using the following Formula (5):

$$C\text{cabin}(t)=C0+[C\text{cabin}(t=0)-C0]\times e^{-t/\tau}$$

$$C0=C\text{outdoor}+\text{CHILDrate}\times\tau \quad (5)$$

Note that in Formula (5), Ccabin represents in-vehicle $CO_2$ concentration, and $\tau$ represents time constant. CHILDrate represents $CO_2$ increase rate, which is a value obtained by dividing the amount of $CO_2$ emitted by a baby or a child present in the vehicle by volume in the vehicle. For example, when a baby having a weight of 10 kg is present in a relatively large wagon, the CHILDrate is approximately 20 ppm/min. Coutdoor represents $CO_2$ concentration outside the vehicle. For example, the Coutdoor can be set to 500 ppm as a fixed value. Alternatively, when the $CO_2$ concentration sensor 2 is arranged near the air intake port of the vehicle, the $CO_2$ concentration outside the vehicle can be measured by taking in outside air through ventilation.

Figure 4:
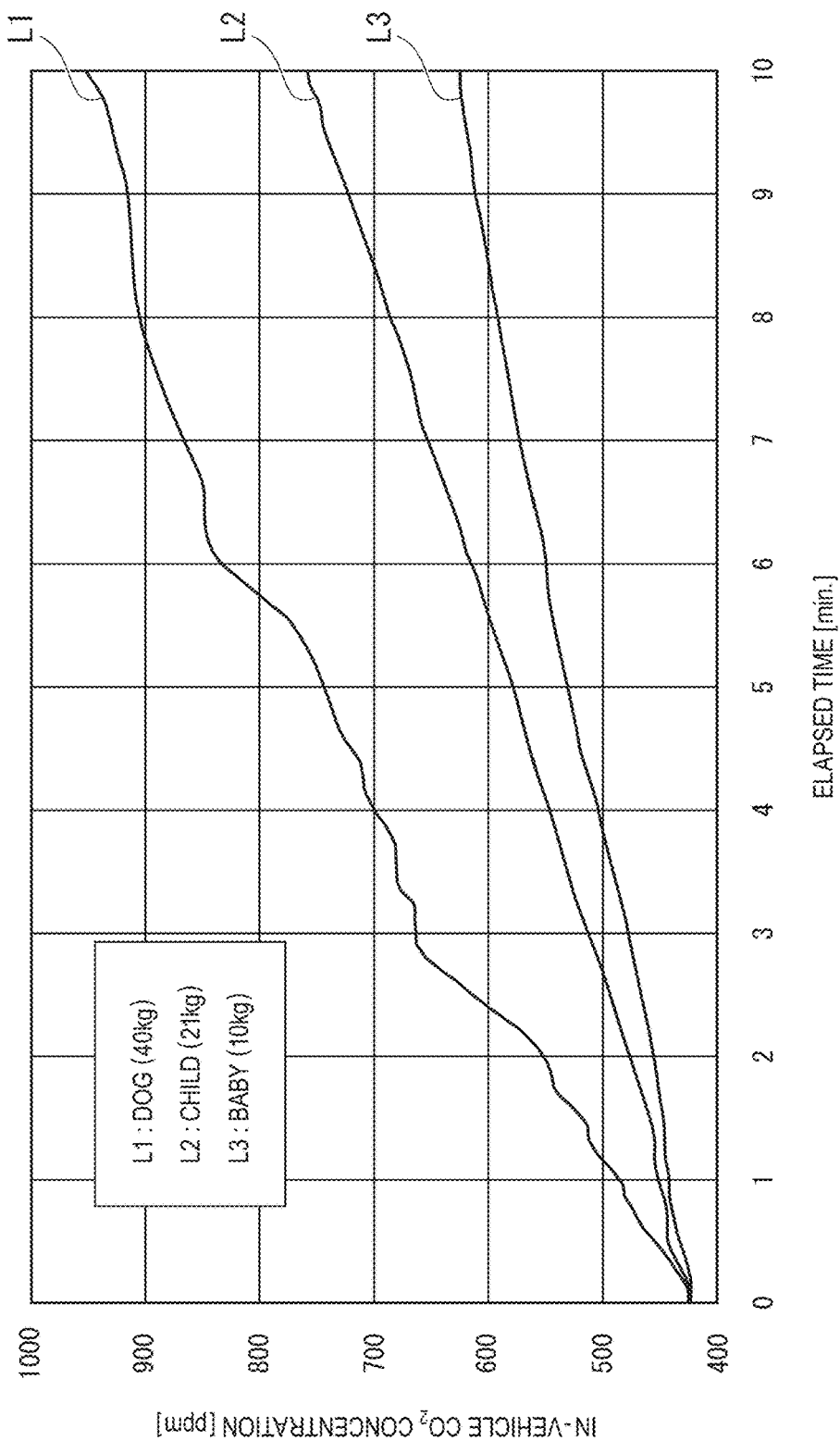
FIG. 4 is a graph illustrating an example of how carbon dioxide concentration changes.

FIG. 4 is a graph illustrating $CO_2$ increase rates of a baby, a child, and a dog when each of them is present in a relatively large wagon vehicle. The horizontal axis of the graph indicates elapsed time (min), and the vertical axis thereof indicates in-vehicle $CO_2$ concentration (ppm). The $CO_2$ increase rate of a baby (characteristic line L3) is 19 ppm/min in the case of a baby having a weight of approximately 10 kg. The $CO_2$ increase rate of a child (characteristic line L2) is 36 ppm/min in the case of a child having a weight of 21 kg. The $CO_2$ increase rate of a dog (characteristic line L1) is 42 ppm/min in the case of a dog having a weight of 40 kg. Incidentally, the presence of two male adults in the vehicle resulted in a $CO_2$ increase rate of 187 ppm/min.

As illustrated in FIG. 4, the $CO_2$ increase rate varies depending on the baby, the child, and the dog, and also varies depending on the weight, the number of people, and the like. Therefore, when detecting the $CO_2$ concentration in a vehicle using the aforementioned Formula (5), it is necessary to detect a $CO_2$ increase rate corresponding to the CHILDrate for each detection target organism, such as the baby, the child, or the dog. Individual differences and the like also need to be considered in order to improve accuracy of the CHILDrate, which is labor intensive. In addition, since the $CO_2$ concentration outside the vehicle varies depending on an environment around the vehicle. Therefore, desirably, $CO_2$ concentration outside the vehicle is actually measured when trying to improve the accuracy of detection of an organism present in the vehicle. This is similarly labor intensive.

On the other hand, in the in-vehicle abnormality detection device 1 according to the first embodiment, the in-vehicle $CO_2$ concentration estimation value C0 is estimated from Formula (1) above. All the other terms except the time constant $\tau$ are values detected by the $CO_2$ concentration sensor 2 after the time point when the parked state is determined, i.e., values that reflect $CO_2$ concentration at the time point of the detection. Then, the time constant $\tau$ is updated on the basis of only the values detected by the $CO_2$ concentration sensor 2 each time it is determined that no organism is present in the vehicle in the determination processing. Thus, the time constant $\tau$ is a value that reflects characteristics of the vehicle such as airtightness at the updated time point. As a result, the $CO_2$ concentration estimation value C0 is estimated on the basis of the time constant $\tau$ according to the characteristics of the vehicle such as airtightness at the present time point and the $CO_2$ concentration at the present time point in this way. This allows for more accurate calculation of in-vehicle $CO_2$ concentration when assuming that the steady state is reached, consequently improving the accuracy of the determination as to whether there is an organism present in the vehicle.

In addition, as described above, the time constant $\tau$ is updated using the detection values of the $CO_2$ concentration sensor 2 after the time point when it is determined that no organism is present in the vehicle in the determination processing. Thus, it is unnecessary to separately acquire information or the like for updating the time constant t, so that the time constant $\tau$ can be easily updated.

Furthermore, when the determination of whether an organism is present in the vehicle is made by comparing $CO_2$ concentration in the vehicle with the threshold value or comparing the increase rate of $CO_2$ concentration in the vehicle with the threshold value, an erroneous determination that there is an organism present therein may be made if the $CO_2$ concentration is higher than the threshold value despite the absence of an organism in the vehicle in a parked state with a relatively high in-vehicle $CO_2$ concentration. Additionally, even when there is an organism present in the vehicle, the increase rate of the $CO_2$ concentration tends to decrease due to a reduced number of people present in the vehicle. This may take some time before determining that the organism is present.

On the other hand, in the first embodiment, the $CO_2$ concentration estimation value C0 is calculated on the basis of a difference value between the detection signal C(0) of the $CO_2$ concentration at the initial time point after parking and the detection signal C(30 s or 90 s) of the $CO_2$ concentration sensor 2 after the predetermined time has elapsed, according to Formula (1) above. Thus, even when the in-vehicle $CO_2$ concentration is relatively high, erroneous determination can be suppressed, enabling more accurate determination.

In addition, as described above, the $CO_2$ concentration estimation value C0, which is the in-vehicle $CO_2$ concentration when assuming the steady state, is estimated, and then the presence or absence of an organism in the vehicle is determined on the basis of the estimated $CO_2$ concentration estimation value C0. Thus, it is possible to determine even when the $CO_2$ concentration in the vehicle does not change actually. For example, the presence of an organism in the vehicle can be detected at the time point when approximately 30 seconds have elapsed since the determination that the vehicle was in the parked state or at the time point when approximately 90 seconds have elapsed since the determination. Accordingly, determination results can be obtained at an earlier stage than when detecting the presence or absence of an organism by comparing the $CO_2$ concentration or the increase rate of the $CO_2$ concentration with the threshold value.

It should be noted that, in the flow chart illustrated in FIG. 3, at step S7, the $CO_2$ concentration change rate $dC(t)/dt$ at the time point t=30 seconds is estimated by setting the time point t1=0 seconds and the time point t2=30 seconds in Formula (1), and using the estimated change rate, the $CO_2$ concentration estimation value C0 at the time point t=30 seconds is estimated, as well as at step S12, the $CO_2$ concentration change rate $dC(t)/dt$ at the time point t=90 seconds is estimated by setting the time point t1=0 seconds and the time point t2=90 seconds in Formula (1), and using the estimated change rate, the $CO_2$ concentration estimation value C0 at the time point t=90 seconds is estimated, but the present invention is not limited thereto.

It suffices that the time points t1 and t2 be different time points when the vehicle is in the parked state. When the time point t2 is later than the time point t1, the time point t2 may be the same as the time point when the $CO_2$ concentration estimation value C0 is estimated (for example, at step S7, the time point t=30 seconds), as illustrated in FIG. 3, or may be different therefrom. Furthermore, at steps S7 and S12, the same $CO_2$ concentration change rate $dC(t)/dt$ may be used to estimate the $CO_2$ concentration estimation value C0.

The flowchart illustrated in FIG. 3 also ends the determination processing after updating the time constant $\tau$ by the processing of step S21. However, when the parked state continues, the time constant $\tau$ may be updated at an optional timing, such as every few hours or every few days, by the same procedure as in the processing of steps S15 to S21.

In addition, the $CO_2$ concentration sensor 2 does not have to be provided exclusively as a sensor for an in-vehicle abnormality detection device. For example, in the case of a vehicle mounted with a $CO_2$ concentration sensor for ventilation control configured to perform ventilation control according to $CO_2$ concentration or an alcohol detector equipped with a $CO_2$ concentration sensor, the $CO_2$ concentration sensor for the alcohol detector may be diverted as the $CO_2$ concentration sensor 2 for an in-vehicle abnormality detection device, or the other $CO_2$ concentration sensor mounted on the vehicle may be diverted as the $CO_2$ concentration sensor for an in-vehicle abnormality detection device.

Second Embodiment

Configuration of In-Vehicle Abnormality Detection Device 1-1

Figure 5:
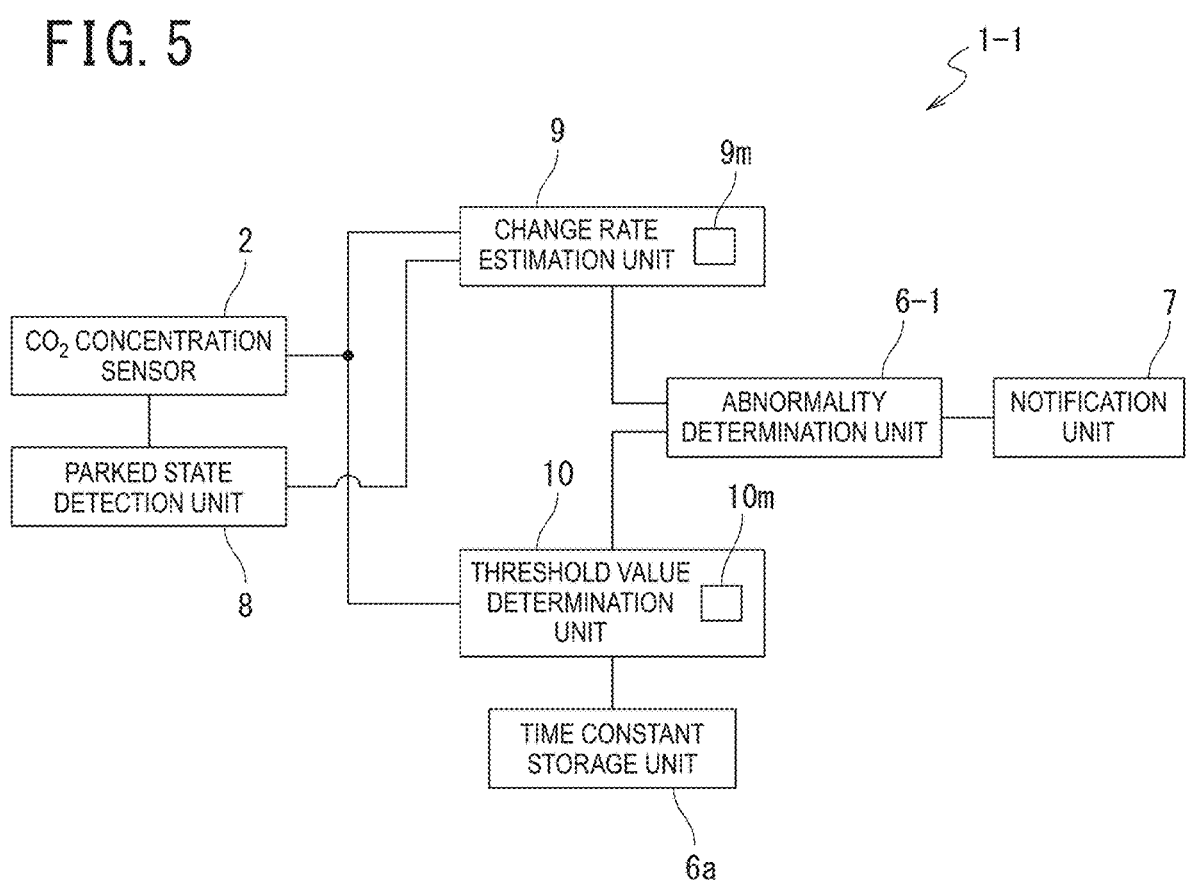
FIG. 5 is a schematic configuration diagram illustrating an example of an in-vehicle abnormality detection device according to the second embodiment of the present invention.

FIG. 5 is a schematic configuration diagram illustrating an example of an in-vehicle abnormality detection device 1-1 according to the second embodiment of the present invention. Note that the same portions as those of the in-vehicle abnormality detection device 1 according to the first embodiment described above are denoted by the same reference signs, and a detailed description thereof is omitted.

The in-vehicle abnormality detection device 1-1 includes the $CO_2$ concentration sensor 2 configured to detect carbon dioxide concentration, a parked state detection unit 8 configured to detect that a vehicle is in a parked state, a change rate estimation unit 9 configured to estimate a change rate of the carbon dioxide concentration in the vehicle at a time point t when the parked state is detected on the basis of detection signals $C(t1)$ and $C(t2)$ of the $CO_2$ concentration sensor at two different time points t1 and t2 (provided that t2>t1) when the parked state is detected by the parked state detection unit 8, a threshold value determination unit 10 configured to determine a threshold value Vth of the change rate of the carbon dioxide concentration on the basis of a detection signal $C(t3)$ of the $CO_2$ concentration sensor at an optional time point t3 when the parked state is detected by the parked state detection unit 8, the time constant τ stored in the time constant storage unit 6a, and the outside-vehicle $CO_2$ concentration Coutdoor, an abnormality determination unit 6-1 configured to determine whether a detection target organism is present in the vehicle according to a result of a comparison between the change rate of the carbon dioxide concentration estimated by the change rate estimation unit 9 and the threshold value Vth determined by the threshold value determination unit 10, and the notification unit 7 configured to notify that the organism is present when the presence of the organism in the vehicle is detected by the abnormality determination unit 6-1.

The parked state detection unit 8 may be achieved by any of the engine off detection unit 3 detecting that the engine is in an off state, the driver detection unit 4 detecting that there is no driver present in the vehicle, or the door state detection unit 5 detecting that all doors of the vehicle are closed of the first embodiment above, or a combination thereof.

The change rate estimation unit 9 estimates the change rate $dC(t)/dt$ of carbon dioxide concentration from the following Formula (6).

The threshold value determination unit 10 determines the threshold value Vth of the change rate of carbon dioxide concentration for determining whether a detection target organism is present in the vehicle from the following Formula (7) using a previously determined parameter K ($0<K≤1$). Then, the threshold value determination unit 10 may determine that the detection target organism is not in the vehicle when $dC(t)/dt<Vth$, and/or may determine that the detection target organism is present in the vehicle when $dC(t)/dt>Vth$.

$$dC(t)/dt=[C(t2)-C(t1)]/(t2-t1) \quad (6)$$

$$Vth=-K\times(C(t3)-Coutdoor)/\tau \quad (7)$$

Here, when the detection target organism is not in the vehicle, a change rate of carbon dioxide concentration expected at an optional time point tx can be represented by the following Formula (8):

$$dC(tx)/dt=-\{[C(t3)-Coutdoor]/\tau\}\cdot G(tx) \quad (8)$$

$G(tx)$ in Formula (8) is represented by the following Formula (9):

$$G(tx)=\exp[-(tx-t3)/\tau] \quad (9)$$

Therefore, at a latest time point tmax allowed to determine whether the detection target organism is present in the vehicle, Formula (8) becomes the following Formulae (10) and (11):

$$dC(tmax)/dt=-\{[C(t3)-Coutdoor]/\tau\}\cdot G(tmax) \quad (10)$$

$$G(tmax)=\exp[-(tmax-t3)/\tau] \quad (11)$$

Here, $G(tmax)$ is clearly $G(tmax)>0$, and t3 is a time point when the parked state is detected, so that tmax t3. Therefore, $G(tmax)$ satisfies the following Formula (12):

$$0<G(tmax)≤1 \quad (12)$$

On the other hand, a specific value of the time constant τ varies depending on the design, condition, and the like of the vehicle body, but is expected to be approximately from 100 minutes to 500 minutes. Additionally, since delayed detection of the detection target organism may affect the health and life or death of the organism, a limit of the tmax that is actually allowed may be approximately from 15 minutes to 30 minutes after the detection of the parked state. Here, since t3 is the time point when the parked state is detected, tmax−t3 is allowed to be at most approximately from 15 minutes to 30 minutes. Here, if τ=150 (minutes) and tmax−t3=15 (minutes), Formula (11) is represented as the following Formula (13), in which $G(tmax)$ is rounded to 1 decimal place, resulting in approximately 0.9.

$$G(tmax)=\exp(-15/150)≈0.9 \quad (13)$$

Additionally, it is usually impossible for the $CO_2$ concentration in the vehicle to be lower than the outside-vehicle $CO_2$ concentration Coutdoor, so that $[C(t3)-Coutdoor]/\tau≥0$. As a result, the following Formula (14) holds.

$$dC(tx)/dt≤dC(tmax)/dt=-\{[C(t3)-Coutdoor]/\tau\}\cdot\exp[-(tmax-t3)/\tau]≈-0.9\cdot\{[C(t3)-Coutdoor]/\tau\} \quad (14)$$

As described above, the coefficient "0.9" in Formula (14) is a design value determined by conditions such as the design and condition of the vehicle body and the time allowed for the detection of a detection target organism. If $G(tmax)$ is assumed to be the design value K (provided that $0<K≤1$) in Formula (14), the following Formula (15) (Formula (7) above) is derived.

$$Vth=-K\cdot\{[C(t3)-Coutdoor]/\tau\} \quad (15)$$

Formula (16) can be obtained from Formula (15) and Formulae (7) and (14) above.

$$dC(tx)/dt≤Vth \quad (16)$$

Accordingly, for example, when Formula (16) is satisfied, it may be determined that there is no detection target organism present in the vehicle. In addition or alternatively, for example, when Formula (16) is not satisfied, it may be determined that the detection target organism is present in the vehicle.

In fact, it is not easy to directly obtain the change rate $dC(tx)/dt$ of the carbon dioxide concentration at an optional time point, so that $dC(tx)/dt$ may be obtained using Formula (6).

Furthermore, in fact, the measured values $C(t1)$ and $C(t2)$ contain noise. Therefore, the value of K may be adjusted in order to avoid erroneous determinations due to the noise. For example, a smaller value may be used as K so that Formula (16) is more easily satisfied. In this case, further assuming that there is a large possibility that the absence of the detection target organism is erroneously determined despite the presence thereof, for example, an additional attempt to detect the detection target organism may be made a plurality of times until a certain period of time elapses since the detection of the parked state. Then, only when the detection target organism is not detected at all times or more often than a certain frequency, the absence of the detection target organism in the vehicle may be determined finally.

In addition, the value K, which is $0<K≤1$, though, may preferably satisfy $0.5<K<1$ since, as described above, τ is expected to be approximately from 100 minutes to 500 minutes, it will be required to complete the detection of the detection target organism within approximately from 15 minutes to 30 minutes after the detection of the parked state, and moreover it is desirable to avoid erroneous determinations due to the noise.

The outside-vehicle $CO_2$ concentration Coutdoor may be a previously determined fixed value. Specifically, a value that is commonly used for carbon dioxide concentration in the atmosphere may be preset as the fixed value. For example, 500 ppm, or 400 ppm that is a typical value of $CO_2$ concentration in a natural environment can be adopted as the fixed value, but these are merely illustrative.

Figure 6:
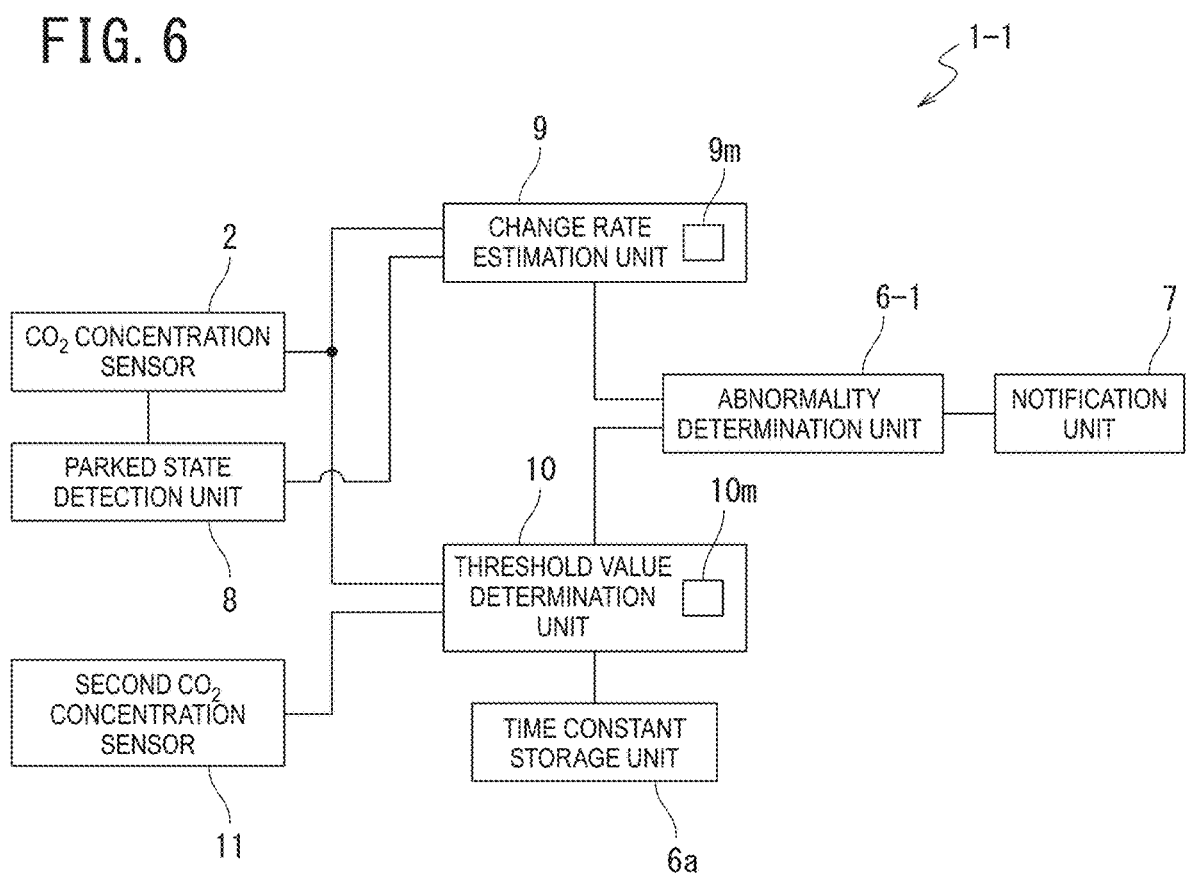
FIG. 6 is a schematic configuration diagram illustrating a modification of the in-vehicle abnormality detection device according to the second embodiment.

In another example, the outside-vehicle $CO_2$ concentration Coutdoor may be a $CO_2$ concentration outside the vehicle obtained by measurement. In this case, as illustrated in FIG. 6, a second $CO_2$ concentration sensor 11 may be further included to measure the outside-vehicle $CO_2$ concentration Coutdoor. Additionally, the second $CO_2$ concentration sensor 11 may be provided at a place that is always exposed to the atmosphere outside the vehicle. Alternatively, the second $CO_2$ concentration sensor 11 may measure $CO_2$ concentration outside the vehicle by taking in the atmosphere outside the vehicle at regular intervals or at an optional timing.

In addition, during the attempt to detect the detection target organism, the C(t1), the C(t2), and the C(t3) need to be retained, for example, in memory. On the other hand, it is not essential that the C(t3) is different from both the C(t1) and the C(t2), so that the time point t3 may preferably be the time point t1 or t2. Setting the time point t3 to the time point t1 or t2 can be effective in reducing the number of values that need to be retained in order to attempt to detect the detection target organism.

Abnormality Determination Processing

Figure 7:
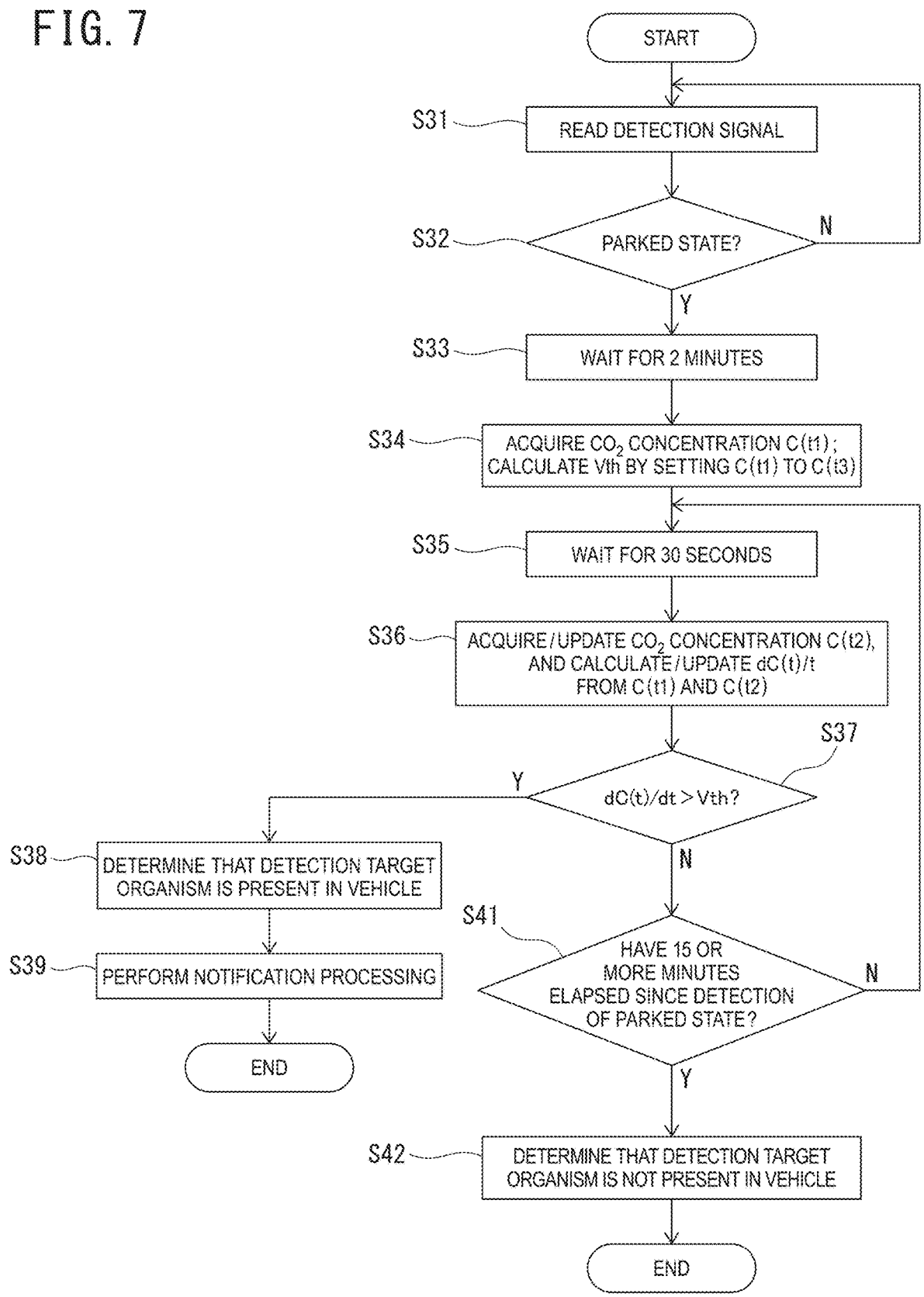
FIG. 7 is a flowchart illustrating an example of a processing procedure of determination processing according to the second embodiment.

Next, an example of a processing procedure of abnormality determination processing executed by the in-vehicle abnormality detection device 1-1 is described with reference to a flowchart of FIG. 7.

The in-vehicle abnormality detection device 1-1 executes the abnormality determination processing at a preset predetermined cycle. First, a detection signal of the parked state detection unit 8 is acquired (step S31). When it is not determined that the vehicle is in a parked state (step S32), the processing ends as it is, whereas when it is determined that the vehicle is in the parked state, the processing proceeds to step S33. Then, a time point when the parked state is determined is set to t=0. A time point when a 2 minute waiting time has elapsed since the time point t=0 is set to t=1, and a detection signal of the $CO_2$ concentration sensor 2 at the time point t=1 is read as C(t1) (step S34). The waiting time in step S33 (2 minutes, here) is set to a time in which fluctuations in the $CO_2$ concentration in the vehicle due to opening and closing of the doors, stop of the circulation fan, disembarkation of the occupant(s), and the like accompanying the parking settle down, and it is possible to acquire an appropriate value as the $CO_2$ concentration in the vehicle.

At step S34, the detection signal C(t1) of the $CO_2$ concentration sensor 2 is updated and stored in a predetermined storage area, for example, a storage unit 9m. Additionally, the detection signal C(t1) is set to C(t3), the time constant $\tau$ previously stored in the time constant storage unit 6a is read, and the threshold value Vth is calculated according to Formula (7) (processing by function of the threshold value determination unit 10). Then, the acquired threshold value Vth is updated and stored in a predetermined storage area, for example, a storage unit 10m.

Next, the processing proceeds to step S35. When a 30 second waiting time has elapsed since the time point t=1, the processing proceeds to step S36. A detection signal C(t2) of the $CO_2$ concentration sensor 2 at the time point t=2 is read and then updated and stored in a predetermined storage area, for example, in the storage unit 9m. The waiting time in step S35 (30 seconds, here) is set to a time in which it is possible to determine that the detection target organism is present in the vehicle from a degree of increase in the $CO_2$ concentration in the vehicle after the parking. Here, for example, approximately 30 seconds is set as an example for the case where the detection target organism is a child, a pet, or the like. Then, the change rate dC(t)/dt of the $CO_2$ concentration in the vehicle is calculated on the basis of Formula (6) using the detection signal C(t1) of the $CO_2$ concentration sensor 2 acquired at step S34 and the detection signal C(t2) of the $CO_2$ concentration sensor 2 acquired at step S36, and updated and stored in a predetermined storage area, for example, the storage unit 9m (processing by function of the change rate estimation unit 9).

Next, the processing proceeds to step S37, where it is determined whether the change rate dC(t)/dt of the $CO_2$ concentration calculated at step S36 is larger than the threshold value Vth set at step S34. When dC(t)/dt>Vth is satisfied, the processing proceeds to step S38, where it is determined that the detection target organism is present in the vehicle, and the notification unit 7 is activated to notify the presence of the organism in the vehicle (step S39) (processing by function of the abnormality determination unit 6-1).

On the other hand, in the processing of step S37, when the change rate dC(t)/dt of the $CO_2$ concentration calculated at step S36 and the threshold value Vth set at step S34 do not satisfy dC(t)/dt>Vth, the processing proceeds to step S41.

At step S41, it is determined whether 15 or more minutes have elapsed since the time point t=0 when the parked state was detected at step S32. When 15 or more minutes have not elapsed, the processing returns to step S35.

Then, at a time point when 30 seconds have elapsed, the processing proceeds to step S36, where the detection signal of the $CO_2$ concentration sensor 2 is read again, and is updated and stored as C(t2) in the predetermined storage area (the storage unit 9m). Then, at step S41, at a time point when 15 or more minutes have elapsed since the time point t=0, the processing proceeds from step S41 to step S42, where it is determined that the detection target organism is not present in the vehicle, and the processing ends.

At step S41, the elapsed time of 15 minutes that has elapsed since the time point t=0, which is a condition for proceeding to step S42 after the determination that the detection target organism is not in the vehicle, is, for example, a time in which if the detection target organism is present in the vehicle, the change rate of the $CO_2$ concentration in the vehicle can be considered to exceed the threshold value Vth before the elapsed time has elapsed at the latest. In other words, the waiting time in step S41 is set to a time in which when the change rate of the $CO_2$ concentration does not exceed the threshold value Vth even at the time point when the elapsed time has elapsed, it can be considered without error that the detection target organism is not present in the vehicle.

Effects of In-Vehicle Abnormality Detection Device 1-1 According to Second Embodiment The in-vehicle abnormality detection device 1-1 according to the second embodiment determines whether the detection target organism is present by comparing the change rate of $CO_2$ concentration in the vehicle obtained from $CO_2$ concentrations in the vehicle at two different time points when the vehicle is in a parked state with the threshold value Vth of the change rate of the $CO_2$ concentration obtained from $CO_2$ concentration in the vehicle at one time point in the parked state, the time constant $\tau$, and the outside-vehicle $CO_2$ concentration Coutdoor. Then, the change rate of the $CO_2$ concentration and the threshold value Vth are calculated using the time constant τ according to characteristics of the vehicle such as airtightness in a state that can be considered to be a steady state. Therefore, the change rate of the CO₂ concentration and the threshold value Vth can be calculated more accurately, resulting in improved accuracy in determining whether there is an organism present in the vehicle.

Figure 8:
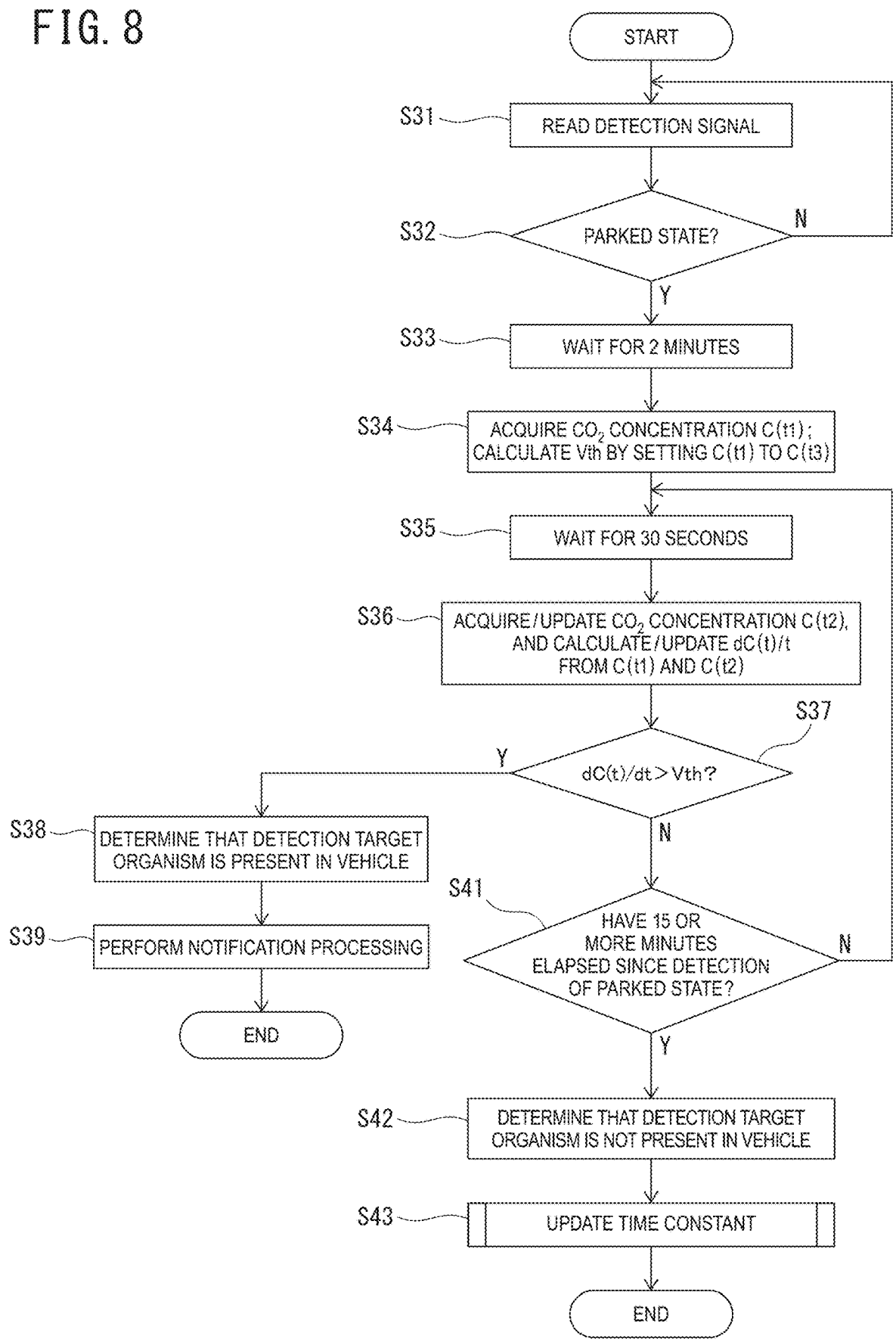
FIG. 8 is a flowchart illustrating a modification of the determination processing according to the second embodiment.

Note that, as illustrated in FIG. 8, even the second embodiment may be configured so that, after it is determined that the detection target organism is not present in the vehicle by the processing of step S42, time constant updating processing (step S43) is executed to update the time constant τ, as in the first embodiment described above. Note that the time constant updating processing (step S43) may be performed in the same manner as the processing of steps S15 to S21 in FIG. 3.

While the embodiments of the present invention have been described hereinabove, each of the above embodiments exemplifies devices and methods for embodying the technological concept of the present invention, and the technological concept of the present invention does not specify materials, shapes, structures, arrangements, and the like of components. The technological concept of the present invention may be modified in various ways within the technological scope defined by the appended claims.

REFERENCE SIGNS LIST

1, 1-1: In-vehicle abnormality detection device
2: $CO_2$ concentration sensor
3: Engine off detection unit
4: Driver detection unit
5: Door state detection unit
6, 6-1: Abnormality determination unit
6a: Time constant storage unit
7: Notification unit
8: Parked state detection unit
9: Change rate estimation unit
10: Threshold value determination unit
11: Second $CO_2$ concentration sensor

The invention claimed is:

1. An in-vehicle abnormality detection device comprising:
a $CO_2$ concentration sensor configured to detect in-vehicle carbon dioxide concentration of a vehicle;
a parked state detection unit configured to detect that the vehicle is in a parked state;
a time constant storage unit configured to store a time constant τ of concentration change of the in-vehicle carbon dioxide concentration;
a change rate estimation unit configured to, on a basis of detection signals $C(t1)$ and $C(t2)$ of the $CO_2$ concentration sensor at two different time points t1 and t2 when the parked state is detected by the parked state detection unit, estimate a change rate of the in-vehicle carbon dioxide concentration at a time point t when the parked state is detected;
a carbon dioxide concentration estimation unit configured to estimate a carbon dioxide concentration estimation value C0 in the vehicle at a time point when a predetermined time has elapsed since the time point t on a basis of a detection signal $C(t)$ of the $CO_2$ concentration sensor at the time point t, the time constant τ stored in the time constant storage unit, and the change rate estimated by the change rate estimation unit; and
an abnormality determination unit configured to determine that there is a detection target organism present in the vehicle when the carbon dioxide concentration estimation value C0 estimated by the carbon dioxide concentration estimation unit is equal to or more than a threshold value set according to the detection target organism.

2. The in-vehicle abnormality detection device according to claim 1, wherein
the change rate estimation unit estimates the change rate $dC(t)/dt$ from the following Formula (1), and
the carbon dioxide concentration estimation unit estimates the carbon dioxide concentration estimation value C0 from the following Formula (2):

$$dC(t)/dt=[C(t2)-C(t1)]/(t2-t1) \quad (1)$$

$$C0=C(t)+\tau \times [dC(t)/dt] \quad (2).$$

3. The in-vehicle abnormality detection device according to claim 1, wherein the time constant τ is determined by airtightness in the vehicle and volume in the vehicle.

4. The in-vehicle abnormality detection device according to claim 1, comprising a time constant updating unit configured to update the time constant τ on a basis of detection signals of the $CO_2$ concentration sensor at a plurality of different time points when it is determined by the abnormality determination unit that the detection target organism is not present in the vehicle.

5. The in-vehicle abnormality detection device according to claim 1, wherein the threshold value is set in plurality according to a type of the detection target organism.

6. The in-vehicle abnormality detection device according to claim 1, further comprising a notification unit configured to notify the presence of the detection target organism in the vehicle when it is determined by the abnormality determination unit that the detection target organism is present in the vehicle.

7. An in-vehicle abnormality detection method comprising:
detecting in-vehicle carbon dioxide concentration of a vehicle when in a parked state by a $CO_2$ concentration sensor;
estimating a change rate of the in-vehicle carbon dioxide concentration at an optional time point when in the parked state on a basis of detection signals of the $CO_2$ concentration sensor at two different time points when in the parked state;
estimating, on a basis of a detection signal of the $CO_2$ concentration sensor at the optional time point, a time constant of concentration change of the in-vehicle carbon dioxide concentration, and the estimated change rate, the in-vehicle carbon dioxide concentration at a time point when a predetermined time according to the time constant has elapsed since the optional time point; and
determining that there is a detection target organism present in the vehicle when the estimated in-vehicle carbon dioxide concentration is equal to or more than a threshold value set according to the detection target organism.

8. An in-vehicle abnormality detection device comprising:
a $CO_2$ concentration sensor configured to detect in-vehicle carbon dioxide concentration of a vehicle;
a parked state detection unit configured to detect that the vehicle is in a parked state;
a time constant storage unit configured to store a time constant τ of concentration change of the in-vehicle carbon dioxide concentration;
a change rate estimation unit configured to, on a basis of detection signals $C(t1)$ and $C(t2)$ of the $CO_2$ concentration sensor at two different time points t1 and t2 (provided that t2>t1) when the parked state is detected by the parked state detection unit, estimate a change rate dC(t)/dt of the in-vehicle carbon dioxide concentration at a time point t when the parked state is detected;

a threshold value determination unit configured to determine a threshold value Vth on a basis of a detection signal C(t3) of the $CO_2$ concentration sensor at a time point t3 when the parked state is detected by the parked state detection unit, the time constant τ stored in the time constant storage unit, and an outside-vehicle $CO_2$ concentration Coutdoor; and an abnormality determination unit configured to determine whether there is a detection target organism present in the vehicle according to a result of a comparison between the change rate of the carbon dioxide concentration estimated by the change rate estimation unit and the threshold value Vth determined by the threshold value determination unit.

9. The in-vehicle abnormality detection device according to claim 8, wherein
the change rate estimation unit estimates the change rate dC(t)/dt from the following Formula (3), and
the threshold value determination unit determines the threshold value Vth from the following Formula (4) using a previously determined parameter K(0<K≤1):

$$dC(t)/dt=[C(t2)-C(t1)]/(t2-t1) \quad (3)$$

$$Vth=-K\times(C(t3)-Coutdoor)/\tau \quad (4).$$

10. The in-vehicle abnormality detection device according to claim 9, wherein the parameter K satisfies 0.5<K<1.

11. The in-vehicle abnormality detection device according to claim 8, wherein the outside-vehicle $CO_2$ concentration Coutdoor is a previously determined fixed value.

12. The in-vehicle abnormality detection device according to claim 8, wherein the outside-vehicle $CO_2$ concentration Coutdoor is given by a second $CO_2$ concentration sensor configured to detect carbon dioxide concentration outside the vehicle.

13. The in-vehicle abnormality detection device according to claim 8, wherein the time point t1 and the time point t3 are a same time point.

14. The in-vehicle abnormality detection device according to claim 8, wherein the time constant τ is determined by airtightness in the vehicle and volume in the vehicle.

15. The in-vehicle abnormality detection device according to claim 8, comprising a time constant updating unit configured to update the time constant τ on a basis of detection signals of the $CO_2$ concentration sensor at a plurality of different time points when it is determined by the abnormality determination unit that the detection target organism is not present in the vehicle.

16. The in-vehicle abnormality detection device according to claim 8, wherein the threshold value is set in plurality according to a type of the detection target organism.

17. The in-vehicle abnormality detection device according to claim 8, further comprising a notification unit configured to notify the presence of the detection target organism in the vehicle when it is determined by the abnormality determination unit that the detection target organism is present in the vehicle.

18. An in-vehicle abnormality detection method comprising:

detecting in-vehicle carbon dioxide concentration of a vehicle when in a parked state by a $CO_2$ concentration sensor;

estimating a change rate of the in-vehicle carbon dioxide concentration at an optional time point when in the parked state on a basis of detection signals of the $CO_2$ concentration sensor at two different time points when in the parked state;

determining a threshold value Vth of the change rate of the in-vehicle carbon dioxide concentration on a basis of a detection signal of the $CO_2$ concentration sensor at the optional time point, a time constant of concentration change of the in-vehicle carbon dioxide concentration, and an outside-vehicle $CO_2$ concentration Coutdoor; and determining whether there is a detection target organism present in the vehicle by comparing the estimated change rate of the in-vehicle carbon dioxide concentration with the threshold value Vth.

* * * * *